United States Patent
O'Neil et al.

[11] Patent Number: 6,063,122
[45] Date of Patent: May 16, 2000

[54] JACK SCREW ADAPTER FOR JOINT PROSTHESIS

[75] Inventors: Michael J. O'Neil, West Barnstable; Arnold Oyola, Taunton; Dennis Sullivan, Sandwich, all of Mass.

[73] Assignee: Johnson & Johnson Professional, Inc., Raynham, Mass.

[21] Appl. No.: 09/102,965

[22] Filed: Jun. 22, 1998

[51] Int. Cl.[7] ........................................................ A61F 2/30
[52] U.S. Cl. .............................................................. 623/18
[58] Field of Search ................................... 623/16, 18, 19, 623/20, 22, 17, 23; 606/88, 89, 90; 433/173

[56] References Cited

U.S. PATENT DOCUMENTS

| | | |
|---|---|---|
| 4,219,893 | 9/1980 | Noiles . |
| 4,301,553 | 11/1981 | Noiles . |
| 4,404,691 | 9/1983 | Buning et al. . |
| 4,578,081 | 3/1986 | Harder et al. . |
| 4,624,673 | 11/1986 | Meyer . |
| 4,714,471 | 12/1987 | Grundei . |
| 4,790,852 | 12/1988 | Noiles . |
| 4,790,854 | 12/1988 | Harder et al. . |
| 4,822,366 | 4/1989 | Bolesky . |
| 4,834,758 | 5/1989 | Lane et al. . |
| 4,846,839 | 7/1989 | Noiles . |
| 4,888,021 | 12/1989 | Forte et al. . |
| 4,904,110 | 2/1990 | Klein . |
| 4,936,853 | 6/1990 | Fabian et al. . |
| 4,944,757 | 7/1990 | Martinez et al. . |
| 4,985,037 | 1/1991 | Petersen . |
| 5,011,496 | 4/1991 | Forte et al. . |
| 5,019,103 | 5/1991 | Van Zile et al. . |
| 5,057,111 | 10/1991 | Park . |
| 5,127,914 | 7/1992 | Calderale et al. . |
| 5,133,760 | 7/1992 | Petersen et al. . |
| 5,137,535 | 8/1992 | Keller . |
| 5,152,796 | 10/1992 | Slamin . |
| 5,194,066 | 3/1993 | Van Zile . |
| 5,269,784 | 12/1993 | Mast . |
| 5,290,313 | 3/1994 | Heldreth . |
| 5,326,359 | 7/1994 | Oudard . |
| 5,330,534 | 7/1994 | Herrington et al. . |
| 5,336,225 | 8/1994 | Zang . |
| 5,370,701 | 12/1994 | Finn . |
| 5,397,360 | 3/1995 | Cohen et al. . |
| 5,405,395 | 4/1995 | Coates . |
| 5,413,605 | 5/1995 | Ashby et al. . |
| 5,556,433 | 9/1996 | Gabriel et al. . |
| 5,609,641 | 3/1997 | Johnson et al. . |
| 5,683,469 | 11/1997 | Johnson et al. . |

FOREIGN PATENT DOCUMENTS

| | | |
|---|---|---|
| 0144667 | 10/1984 | European Pat. Off. . |
| 0307655 | 8/1988 | European Pat. Off. . |
| 0529408 | 3/1993 | European Pat. Off. . |
| 0531263 | 3/1993 | European Pat. Off. . |
| 0621019 | 2/1994 | European Pat. Off. . |
| 0473375 | 3/1992 | Germany . |
| 1575278 | 5/1978 | United Kingdom . |
| 2259253 | 8/1992 | United Kingdom . |
| 9709939 | 3/1997 | WIPO . |

OTHER PUBLICATIONS

Johnson & Johnson Orthopaedics Research & Development "P.F.C.® *Modular Knee System Research Data and Laboratory Testing*," cover and pp. 8, 36 and 37 (1989).

*Primary Examiner*—Jeffrey A. Smith
*Assistant Examiner*—Eduardo C. Robert
*Attorney, Agent, or Firm*—Nutter, McClennen & Fish LLP

[57] ABSTRACT

The present invention provides a jack device that is a body interposable between prosthetic joint components to provide a selectable spacing between them, and to thereby ensure that rotatably mated components are secured together in a selected angular orientation.

20 Claims, 2 Drawing Sheets

6,063,122

JACK SCREW ADAPTER FOR JOINT PROSTHESIS

CROSS-REFERENCE TO RELATED APPLICATIONS

Not applicable.

STATEMENT REGARDING FEDERALLY SPONSORED RESEARCH

Not applicable.

FIELD OF THE INVENTION

The invention relates to medical devices, and more particularly to prosthetic, joint components such as knees.

BACKGROUND OF THE INVENTION

Joint arthroplasty is a well-known surgical procedure by which a diseased and/or damaged natural joint is replaced by a prosthetic joint. Typical prostheses include several components that can be joined together in various combinations and orientations to provide a desired joint configuration. Such a modular system significantly reduces the number of individual components that must be purchased, stocked, and used during a surgical procedure.

Components, however, can sometimes be challenging to mate in a secure manner, while maintaining a precise, selected orientation of one component with respect to another. For example, with threaded components it is very difficult to precisely mate a slotted stem to another prosthetic component and ensure that the slot is oriented in a desired direction with respect to the other component when the threads are screwed tight. If the slot is misaligned, the performance of the prosthetic joint can be seriously degraded in situ, and/or be difficult to install.

Therefore, despite the existence of joint prostheses having modular components, there remains a need for a modular joint prosthesis that has greater versatility to accommodate differing patient anatomy and joint conditions. It is thus an object of the invention to provide a modular prosthesis having greater versatility to accommodate different patient anatomy and joint conditions while maintaining a relatively low component count. It is another object of the invention to provide a modular prosthesis having components that are physiologically and geometrically compatible with different anatomical conditions. Other general and more specific objects of the invention will in part be apparent from the drawings and description that follow.

BRIEF SUMMARY OF THE INVENTION

The present invention overcomes the shortcomings of the prior art by providing a jack device that enables rotatably mated components to be secured in a selected angular orientation through application of a tension force on threads.

In an exemplary embodiment, a jack device is a body interposable between prosthetic joint components to provide a selectable spacing between them. The jack device can be securable to one of the components to selectively increase or decrease its length. The jack device can include a proximal portion insertable within one of the components and a distal portion that extends from the component for mating with another component. Also, the jack device can be rotatably engagable with a first component and the first component can be rotatably engagable with a second component. The jack device and the components can include complimentary threaded surfaces for mating.

In an illustrative embodiment of a joint prosthesis having a jack device, the joint prostheses includes a stem, a prosthetic component, and a jack Therefore, despite the existence of joint prostheses having modular components, there remains a need for a modular joint prosthesis that has greater versatility to accommodate differing patient anatomy and joint conditions. It is thus an object of the invention to provide a modular prosthesis having greater versatility to accommodate different patient anatomy and joint conditions while maintaining a relatively low component count. It is another object of the invention to provide a modular prosthesis having components that are physiologically and geometrically compatible with different anatomical conditions. Other general and more specific objects of the invention will in part be apparent from the drawings and description that follow.

BRIEF SUMMARY OF THE INVENTION

The present invention overcomes the shortcomings of the prior art by providing a jack device that enables rotatably mated components to be secured in a selected angular orientation through application of a tension force on threads.

In an exemplary embodiment, a jack device is a body interposable between prosthetic joint components to provide a selectable spacing between them. The jack device can be securable to one of the components to selectively increase or decrease its length. The jack device can include a proximal portion insertable within one of the components and a distal portion that extends from the component for mating with another component. Also, the jack device can be rotatably engagable with a first component and the first component can be rotatably engagable with a second component. The jack device and the components can include complimentary threaded surfaces for mating.

In an illustrative embodiment of a joint prosthesis having a jack device, the joint prostheses includes a stem, a prosthetic component, and a jack device. The stem has a proximal end and a distal end, and the proximal end has threaded surfaces that define a cavity. The prosthetic component has a proximal end, a distal end, and a bore through the prosthetic component that is open at the distal end and the proximal end. At least a portion of the bore and the exterior surface is threaded, and the distal end of the prosthetic component is insertable within the cavity of the stem and threadably engagable therewith. The jack screw has a threaded exterior surface region and is insertable within the bore of the prosthetic component and threadably engagable therewith.

BRIEF DESCRIPTION OF THE DRAWINGS

A more complete understanding of the present invention and the attendant advantages and features thereof will be more readily understood by reference to the following detailed description when considered in conjunction with the accompanying drawings wherein.

DETAILED DESCRIPTION OF THE INVENTION

Figure 1:
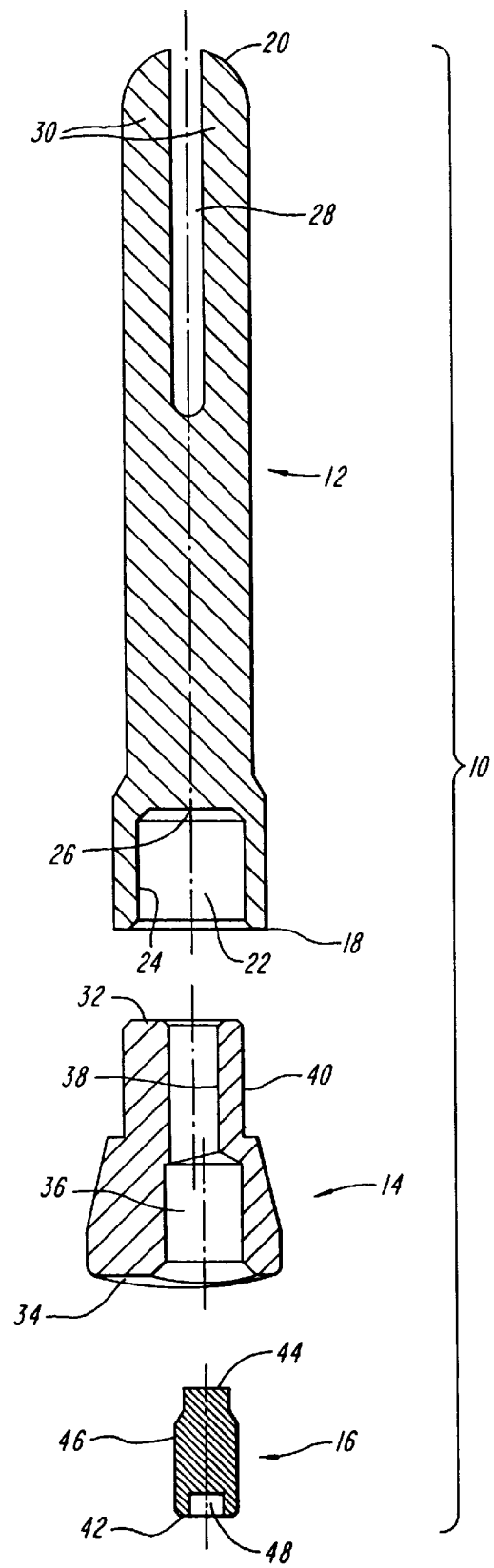
FIG. 1 is an exploded view of a multi-piece prosthetic joint component shown in cross section.

FIG. 1 is an exploded view of a multi-piece prosthetic joint component 10, shown in cross section, that includes a stem 12, a prosthetic component 14, and a jack device 16.

The stem 12 has a proximal end 18 and a distal end 20. The proximal end 18 defines a cavity 22 open at the proximal end of the stem. The cavity 22 is bounded by threaded side surfaces 24 and a distal wall 26. The stem 12 is furcated at its distal end 20, wherein a slot or space 28 separates two tines 30 that may be flexible.

The prosthetic component 14 is matable with the stem 12 and includes a proximal end 32, a distal end 34, and a bore 36 through the prosthetic component that is open at the distal end and the proximal end. At least a portion of a wall 38 that defines the bore 36 is threaded. Also, at least a portion of an exterior surface 40 of the prosthetic component 14 is provided with threads that are complimentary to the threads of the side surfaces 24 that define the cavity 22 of the stem 12. Thus, the distal end 32 of the prosthetic component 14 is insertable within the cavity 22 of the stem 12 and is threadably engagable with the threaded side surfaces 24 of the stem to draw the distal end of the prosthetic component toward the distal wall 26 of the cavity.

The jack device 16 is interposable between the stem 12 and the prosthetic component 14 to provide a selectable spacing between the distal wall 26 of the cavity 22 in the stem 12 and the distal end 32 of the prosthetic component. Depending upon the positioning of the jack device 16 with respect to the prosthetic component 14 and the stem, the length of the assembled prosthetic joint component 10 can be adjusted and locked through tension applied to threads.

In an exemplary embodiment, the jack device is configured as a jack screw having a proximal end 42, a distal end 44, and a threaded exterior surface 46. The proximal end 42 can include a tool engagement feature 48, such as a slot to locate and/or receive a tool such as a screwdriver or an Allen wrench (not shown). Thus, the jack device 16 can be rotated with respect to the prosthetic component 14 such that the complimentary threads engage and the distal end 44 of the jack device protrudes a selected distance from the distal end 32 of the prosthetic component. Tension on the threads between the prosthetic component 14 and the stem 12 caused by the jack device pushing against the distal wall 26 of the stem prevents them from rotating. Alternatively, the jack device 16 can be forced through the bore 36 and held in place with respect to the prosthetic component 14 by a friction or interference fit.

When the stem 12 is mated to the prosthetic component 16, the jack device 16 can be extended from the distal end 32 of the prosthetic component until the distal end 44 of the jack device abuts the distal wall 26 of the stem.

Not only does the jack device 16 allow the overall length of the prosthetic joint component 10 to be selected, it also allows the angular orientation of the stem 12, and thus the slot 28, to be selected with respect to a selected point on the prosthetic component 14.

For example, the prosthetic joint component 10 can be assembled by inserting the distal end 32 of the prosthetic component 14 into the cavity 22 of the stem, and rotating the prosthetic component with respect to the stem until they are firmly joined and the slot is aligned with a selected point on the prosthetic component. A jack device 16 is then inserted through the bore 36 in the prosthetic component 14 until the distal end 44 of the jack device abuts the distal wall 26 of the stem 12. Even if there is thread path available to allow the stem 12 and the prosthetic component 14 to be drawn closer together, the jack device 16 inhibits such movement. Thus, the slot 28 remains aligned with the selected point on the prosthetic component 14. If the jack device 16 is a jack screw, a Spiralock thread form can be used in both threads to lock the components in place.

A modular prosthetic joint system provides many opportunities for a surgeon to customize the joint for various patient requirements, and the jack device 16 allows various sized and shaped prosthetic components, possibly having different functions, to be mated to a second component, such as a stem that must be inserted into a prepared intramedullary cavity in a particular orientation. FIGS. 2–6 illustrate various examples.

Figure 2:
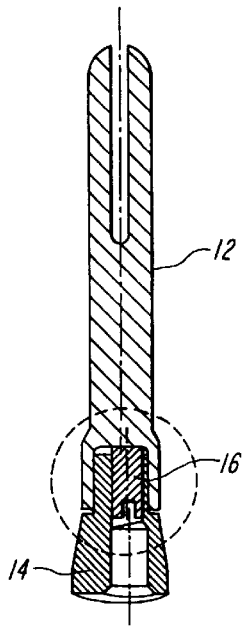
FIG. 2 is a sectional view of the prosthetic joint component of FIG. 1, showing the pieces in an assembled configuration.

FIG. 2 is a sectional view of the prosthetic joint component of FIG. 1, showing the stem 12, prosthetic component 14, and the jack device 16 in an assembled configuration. In this example, the prosthetic component 14 is a stem extension element.

Figure 3:
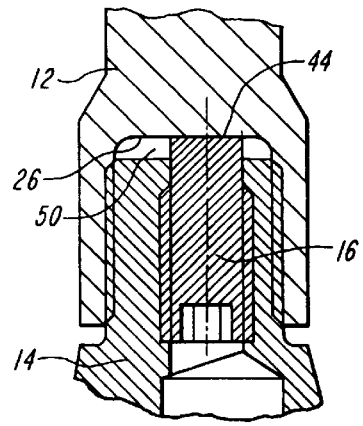
FIG. 3 is a detailed view of a portion of the assembled component of FIG. 2.

FIG. 3 is a detailed view of a portion of the assembled prosthetic joint component of FIG. 2. In this view, the jack device 16 and the stem are mated to the stem extension element 14. The distal end 44 of the jack device 16 abuts the distal wall 26 of the stem 12 to maintain a separation between the stem and the stem extension element 14, as shown by a space 50, thereby ensuring that the stem 12 and slot are not over-rotated. This is important because threaded connections are preferable to pieces that are hammered together. Another advantage provided by the jack device 16 is that a single stem configuration can be used with a variety of different components. Also, because the jack device 16 is loaded in compression (not tension), the likelihood of component failure is reduced.

Figure 4:
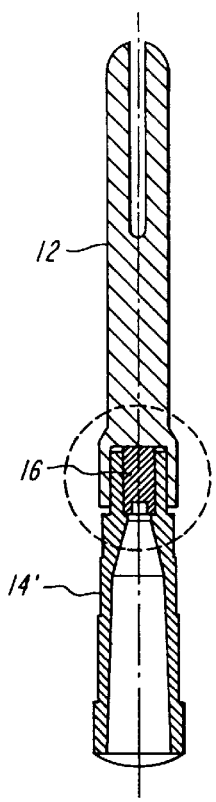
FIG. 4 is a sectional view of another prosthetic joint component, showing the pieces in an assembled configuration.

FIG. 4 is a sectional view of a prosthetic joint component of FIG. 1, showing the stem 12, a prosthetic component 14', and the jack device 16 in an assembled configuration. In this example, the prosthetic component 14' is a femoral sleeve.

Figure 5:
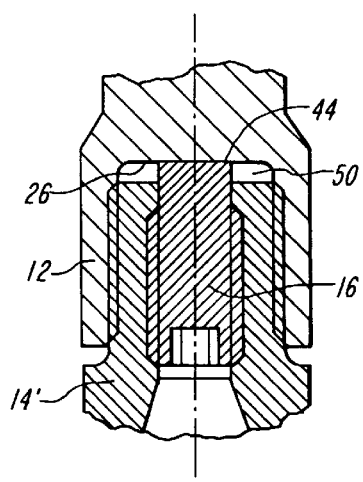
FIG. 5 is a detailed view of a portion of the assembled component of FIG. 4.

FIG. 5 is a detailed view of a portion of the assembled prosthetic joint component of FIG. 4. In this view, the jack device 16 and the stem 12 are mated to the femoral sleeve 14'. The distal end 44 of the jack device 16 abuts the distal wall 26 of the stem 12 to maintain a separation between the stem and the femoral sleeve 14' as shown by a space 50.

Figure 6:
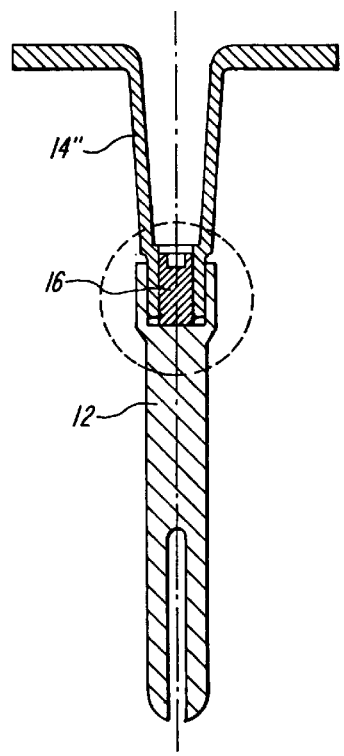
FIG. 6 is a sectional view of yet another prosthetic joint component, showing the pieces in an assembled configuration.

FIG. 6 is a sectional view of a prosthetic joint component, showing the stem 12, a prosthetic component 14", and the jack device 16 in an assembled configuration. In this example, the prosthetic component 14" is a tibial tray.

Figure 7:
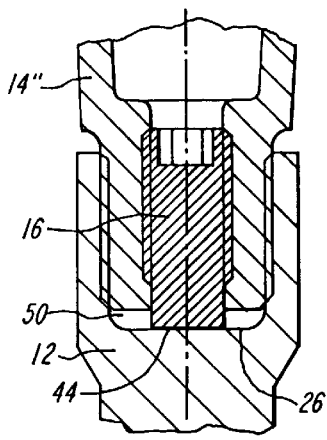
FIG. 7 is a detailed view of a portion of the assembled component of FIG. 6.

FIG. 7 is a detailed view of a portion of the assembled prosthetic joint component of FIG. 6. In this view, the jack device 16 and the stem 12 are mated to the tibial tray 14". The distal end 44 of the jack device 16 abuts the distal wall 26 of the stem 12 to maintain a separation between the stem and the tibial tray as shown by a space 50.

A variety of modifications and variations of the present invention are possible in light of the above teachings. All references cited herein are expressly incorporated by reference in their entirety.

What is claimed is:

1. A joint prosthesis system, comprising:
   a first component having a length;
   a second component, wherein the first component is directly mated to the second component; and
   a jack device rotatable engaged with the first component to provide a selectable spacing between the first component and the second component, and wherein the first component includes a threaded surface that is engaged with complementary threads of the second component.

2. The joint prosthesis system of claim 1, wherein the jack device is adapted to selectively increase or decrease the length of the first component.

3. The joint prosthesis system of claim 2, wherein the jack device has a proximal portion and a distal portion, and wherein at least the proximal portion is inserted within the first component to permit the distal portion to extend from the first component.

4. The joint prosthesis system of claim 3, wherein the distal portion of the jack device includes an abutment surface that contacts the second component when the distal portion of the jack device extends a predetermined distance from the first component.

5. The joint prosthesis system of claim 4, wherein the proximal portion of the jack device includes a tool engagement feature.

6. The joint prosthesis system of claim 1, wherein the jack device includes a threaded exterior surface region.

7. A joint prosthesis comprising:
   a stem having a proximal end and a distal end, the proximal end having threaded surfaces that define a cavity;
   a prosthetic component having a proximal end, a distal end, and a bore through the prosthetic component that is open at the distal end and the proximal end, wherein at least a portion of the bore is threaded, wherein at least a portion of an exterior surface of the prosthetic component is threaded, and wherein the distal end is insertable within the cavity and threadably engagable with the threaded surfaces of the stem; and
   a jack screw having a threaded exterior surface region, the jack screw being insertable within the bore and threadably engagable with the threaded portion of the bore.

8. The joint prosthesis of claim 7, wherein the prosthetic component is a tibial tray.

9. The joint prosthesis of claim 7, wherein the prosthetic component is a sleeve.

10. The joint prosthesis of claim 7, wherein the prosthetic component is a femoral adapter.

11. The joint prosthesis of claim 7, wherein the stem is rotatably engagable with the prosthetic component.

12. The joint prosthesis of claim 7, wherein the jack screw has a proximal portion and a distal portion, and wherein the proximal portion is insertable within the bore and the distal portion is extendable from the prosthetic component.

13. The joint prosthesis of claim 12, wherein the distal portion of the jack screw includes an abutment surface that contacts the stem when the distal portion of the jack screw extends a predetermined distance from the prosthetic component.

14. The joint prosthesis of claim 13, wherein the proximal end of the jack device includes a tool engagement feature.

15. The joint prosthesis of claim 13, wherein the abutment surface of the of the jack screw is pressed against the stem to create tension between the stem and the prosthetic component.

16. The joint prosthesis of claim 15, wherein the stem is slotted.

17. A joint prosthesis comprising:
   a stem having a proximal end and a slotted distal end, the proximal end having threaded surfaces that define a cavity;
   a prosthetic component rotatably engagable with the stem, the prosthetic component having a proximal end, a distal end, and a bore through the prosthetic component that is open at the distal end and the proximal end, wherein at least a portion of the bore is threaded, wherein at least a portion of an exterior surface of the prosthetic component is threaded, and wherein the distal end is insertable within the cavity and threadably engagable with the threaded surfaces of the stem; and
   a jack screw having a threaded exterior surface region, the jack screw being insertable within the bore and threadably engagable with the threaded portion of the bore.

18. The joint prosthesis of claim 17, wherein the prosthetic component is a femoral adapter.

19. The joint prosthesis of claim 17, wherein the prosthetic component is a sleeve.

20. The joint prosthesis of claim 17, wherein the prosthetic component is a tibial tray.

* * * * *